United States Patent
Makdissi

(10) Patent No.: US 9,592,394 B2
(45) Date of Patent: Mar. 14, 2017

(54) ACTIVE IMPLANTABLE MEDICAL DEVICE WITH CYCLE TO CYCLE CAPTURE DETECTION

(71) Applicant: SORIN CRM SAS, Clamart (FR)

(72) Inventor: Alaa Makdissi, Paris (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 14/951,704

(22) Filed: Nov. 25, 2015

(65) Prior Publication Data

US 2016/0151632 A1    Jun. 2, 2016

(30) Foreign Application Priority Data

Nov. 28, 2014  (FR) ...................... 14 61632

(51) Int. Cl.
| | |
|---|---|
| *A61N 1/00* | (2006.01) |
| *A61N 1/37* | (2006.01) |
| *A61N 1/375* | (2006.01) |
| *A61N 1/372* | (2006.01) |
| *A61N 1/365* | (2006.01) |

(52) U.S. Cl.
CPC ......... *A61N 1/3712* (2013.01); *A61N 1/3756* (2013.01); *A61N 1/36578* (2013.01); *A61N 1/37205* (2013.01)

(58) Field of Classification Search
CPC .............. A61N 1/36578; A61N 1/3712; A61N 1/37205; A61N 1/3756
See application file for complete search history.

(56) References Cited

U.S. PATENT DOCUMENTS

| | | |
|---|---|---|
| 5,549,652 A | 8/1996 | McClure et al. |
| 6,650,940 B1 | 11/2003 | Zhu et al. |
| 2008/0021336 A1 | 1/2008 | Dobak, III |
| 2010/0125309 A1* | 5/2010 | Casset ............... A61N 1/3712 607/28 |

FOREIGN PATENT DOCUMENTS

| | | |
|---|---|---|
| EP | 2 189 182 | 5/2010 |
| EP | 2 412 401 A1 | 2/2012 |
| WO | WO-2005/089866 A1 | 9/2005 |

OTHER PUBLICATIONS

Preliminary Search Report for French Patent Application No. 1461632, dated May 21, 2015, 2 pages.

* cited by examiner

*Primary Examiner* — George Manuel
(74) *Attorney, Agent, or Firm* — Foley & Lardner LLP

(57) ABSTRACT

The invention relates to a device incorporating an endocardial acceleration (EA) sensor. A capture test circuit of the device collects a sampled EA signal and extracts a limited series of EA measurements during a duration of a predetermined temporal window opened after delivery of a pacing pulse. An indicator value based on an average of absolute values of successive EA measurements of the series of EA measurements is calculated at an end of the temporal window. The indicator value is compared to a predetermined discrimination threshold to determine the presence or absence of a capture according to whether the indicator value lies above or below the predetermined discrimination threshold. The indicator value is very robust to noise and particularly efficient in terms of computing, which reduces, in large proportions, consumption of the digital processor and thus of the capsule.

12 Claims, 6 Drawing Sheets

ACTIVE IMPLANTABLE MEDICAL DEVICE WITH CYCLE TO CYCLE CAPTURE DETECTION

CROSS-REFERENCE TO RELATED PATENT APPLICATIONS

This application claims the benefit of and priority to French Patent Application No. 1461632, filed Nov. 28, 2014, which is incorporated herein by reference in its entirety.

BACKGROUND

The invention relates to "active implantable medical devices" as defined by the Directive 90/385/EEC of 20 Jun. 1990 of the Council of the European Communities, and particularly implantable devices that continuously monitor the heart rate and if necessary deliver electrical stimulation, resynchronization and/or defibrillation pulses to the heart when a rhythm disorder is detected by the device.

The disclosure relates to devices that are autonomous capsules intended to be implanted in a heart chamber, especially a ventricle. These capsules are free of any mechanical connection to an implantable main device (e.g., a housing of the stimulation pulse generator) or non-implantable main device (e.g., an external device such as a programmer or monitoring device for patient remote monitoring). These devices are called "leadless capsules" to distinguish them from electrodes or sensors disposed at the distal end of a conventional probe (lead), which is traversed throughout its length by one or more conductors galvanically connecting the electrode or sensor to a generator connected to an opposite, proximal end of the lead. A detection/stimulation electrode in contact with the wall of the ventricle enables it to detect the presence or absence of a spontaneous depolarization wave of the cardiac cavity, as well as the time of occurrence of this wave (ventricular or atrial marker).

The electrode also allows the delivery of a stimulation pulse in the event of absent or late spontaneous depolarization to cause contraction of the cardiac cavity.

Note, however, that the autonomous nature of the capsule is not inherently a necessary feature of the present disclosure.

The management of stimulation energy is a critical aspect of any implantable pacemaker, because it has a direct impact on the power consumption of a battery, and thus on its overall lifespan.

Power consumption is particularly critical in the case of a leadless capsule where, unlike conventional pacemakers, the energy required for the issuance of stimulation is 70% of the total energy consumed. In addition, the very small dimensions of the leadless capsule impose restrictions on the size of the battery and thus the capacity, as the battery in the leadless capsule often occupies more than 70% of the volume of the device.

In fact, if it was possible to reduce, for example, half the energy required for stimulation, then the size of the battery could be reduced by about 40% while keeping the same longevity, which would reduce the volume of the capsule to about 0.6 cm$^3$ (against 1 cm$^3$ in the best case today), with all performances being equal.

To minimize the energy dedicated to stimulation as much as possible, while maintaining the effectiveness of delivered electrical pulses, a technique called "cycle to cycle capture" may be employed, which maintains the stimulation energy at a minimum level continuously checking, if the stimulation was effective ("capture") or not, after each stimulation. If no depolarization wave has been induced by stimulation of the cardiac cavity (non-capture), the implant delivers, during the same cardiac cycle, a stimulation of a relatively high energy to ensure the triggering of a depolarization. Then, by successive iterations, the stimulation energy is gradually reduced in each cardiac cycle, to converge to an energy close to a limit or "triggering threshold" needed to cause depolarization of the cardiac cavity.

Various capture test techniques have been proposed. A signal provided by a sensor directly detecting the mechanical contraction of the myocardium can be used, which allows information about the response of the cardiac cavity to stimulation to be obtained immediately, disregarding the blanking periods and other limitations inherent to the collection of an electric signal. In other words, the purpose is to use a functional signal representative of cardiac mechanics, instead of a signal originating from the electrical propagation of a depolarization wave.

EP 2412401 A1 (Sorin CRM) describes such a device including ventricular capture test methods operating by analysis of an endocardial acceleration (EA) signal. The EA signal can be collected by an endocardial lead equipped with a distal pacing electrode implanted into the ventricle, incorporating a microaccelerometer for measuring endocardial acceleration.

The capture test is based on the analysis of the EA signal, including its successive components (EA components) corresponding to the main heart sounds that are possible to recognize in each cardiac cycle (S1 and S2 sounds of a phonocardiogram). Amplitude variations of a first component (EA1 component) are closely related to changes in pressure in the ventricle, while a second component (component EA2) occurs during the isovolumetric ventricular relaxation phase. The analysis can also take into account the secondary component (called EA4 or EA0 component) produced by a contraction of the atrium, as in the case of EP 2189182 A1 (Sorin CRM), which describes a device provided with analysis methods for recognizing the presence (or absence) of a EA4 component in the EA signal in order to deduce the presence (or absence) of a contraction of the atrium, subsequent to an application of an electrical pulse to the latter by the atrial pacing methods.

For the ventricular capture test described by EP 2412401 A1 cited above, the EA1 and EA2 components of the EA signal are analyzed to extract various relevant parameters such as the peak-to-peak amplitude PEA1 and PEA2 of the EA1 and EA2 components, the temporal interval between the PEA1 and PEA2 peaks, the half height width of the components EA1 and/or EA2, the instants of beginning and of end of these components, etc. The parameters extracted may also be morphological parameters representative of the waveform of the EA signal or of its envelope.

In the technique described by EP 2412401 A1 cited above, the different parameters are calculated and grouped as a representative vector, creating a point of a multidimensional vector space. The vector space is then analyzed by application of classification algorithms to determine a boundary in the vector space between capture and non-capture. For each cycle, a parameter vector is formed from the collected EA signal and the position of the parameter vector in the vector space is evaluated to determine whether capture is present or absent.

This type of ventricular capture test is very powerful. However, its implementation, by complex algorithms of signal analysis and classification in a multidimensional space, involves complex numerical calculations, resulting in high consumption of the implant processor, typically on the order of 2 µW (which is compared with the energy is consumed for the delivery of stimulation, on the order of 5 µW).

To significantly reduce the consumed energy, especially for a leadless capsule pacemaker, the problem is to find a method of verification of the cycle to cycle ventricular capture that not only reduces energy stimulation to a minimum, but also does not increase the consumption of the electronic circuit, in particular of the digital processor.

It is desirable that the consumption of the electronics associated with the cycle to cycle capture test function does not exceed a few hundreds of nanowatts. In fact, if the energy dedicated to stimulation can also be reduced at a value of 1 µW to 2 µW (depending on the level of the stimulation threshold), the size of the battery can be reduced 40-60% compared to that of current devices.

Other capture verification techniques by implementation of a detection of the mechanical contraction of the heart are described in particular in U.S. Pat. No. 5,549,652 (a cycle to cycle capture test, but without detailed description of a specific method) and U.S. Pat. No. 6,650,940 B1 (a periodic conventional capture test by gradual reduction of energy over several cycles).

SUMMARY

One object of the invention is to provide a ventricular capture detection technique that minimizes the number of digital computer operations necessary and, consequently, power consumption of the implant processor.

The disclosure provides a device including:
a ventricular stimulation circuit adapted to deliver low energy pacing pulses to an implantable electrode located within a ventricle of a patient;
an acceleration sensor, capable of delivering/generating an endocardial acceleration EA signal; and
a ventricular capture detection circuit adapted to detect, by analysis of the EA signal during a cardiac cycle, the presence or absence of a contraction of the ventricle subsequent to the application of a stimulation pulse, where the ventricular capture detection circuit includes a processor configured to:
sample the EA signal delivered by the sensor, generating successive sampled EA measurements; and
extract a plurality of the sampled EA measurements during the duration of a predetermined temporal window starting after the delivery of a pacing pulse.

The processor of the ventricular capture detection circuit is further configured to:
calculate, by summation, an indicator value of an average of the absolute values of successive EA measurements of the series of EA measurements at the end of the temporal window; and
compare the calculated indicator value to a predetermined discrimination threshold, and determine the presence or absence of ventricular capture depending on whether the indicator value is above or below the predetermined discrimination threshold.

According to various advantageous subsidiary characteristics:
the calculation of the indicator value is made independently of the values of the peak-to-peak amplitude of the peaks of the EA signal;
the duration of the predetermined temporal window is between 75 and 350 ms, and/or the start time of the predetermined temporal window is between 5 and 100 ms after delivery of the stimulation pulse;
the processor is further configured to disable the ventricular capture detection circuit after the end of the temporal window until the beginning of the temporal window of the next cardiac cycle, and deactivate the ventricular capture detection circuit between two successive samplings of the EA signal delivered by the sensor;
the calculation by summation of the indicator value includes:
calculating the indicator value from a number of successive EA measurements that is a constant number from one cardiac cycle to another;
summing the absolute values of the successive EA measurements of the series of EA measurements;
summing the absolute values of the respective differences between: i) the successive EA measurements of the EA series of EA measurements and ii) a value that is an average of the EA measurements of the series of EA measurements;
summing the absolute values of the respective differences between: i) the successive EA measurements of the series of EA measurements and ii) a base line constant; or
summing the absolute values of respective differences between: i) the successive EA measurements of the series of EA measurements and ii) the value of the first EA measurement of the series of EA measurements;
the processor is further configured to initialize determining the discrimination threshold, the determination including controlling the ventricular stimulation circuit to output a succession of pacing pulses at maximum power; calculating an average of the respective indicator values of the sequence of pacing pulses at maximum power; applying a reduction factor to the calculated average of the indicator values and issuing the result as the value of the discrimination threshold.

BRIEF DESCRIPTION OF THE DRAWINGS

Further features, characteristics and advantages of the present disclosure will become apparent to a person of ordinary skill in the art from the following detailed description of preferred embodiments of the present invention, made with reference to the drawings annexed, in which like reference characters refer to like elements and in which.

DETAILED DESCRIPTION

An exemplary embodiment of a device of the invention will now be described.

Regarding its software aspects, the invention may be implemented by appropriate programming of controlling software of a known cardiac pacemaker, for example an endocardial leadless capsule.

These devices include a programmable microprocessor provided with circuits for shaping and delivering stimulation pulses to implanted electrodes. Using telemetry, it is possible to transmit software that will be stored in memory and executed by the device to implement the functions of an embodiment of the invention which will be described below. The adaptation of these devices to implement the functions of the disclosure is within the reach of a skilled-in-the-art person and will not be described in detail. In particular, software stored in memory and executed can be adapted and used to implement the functions of the disclosure which will be described below.

A method of an embodiment of the invention may be implemented primarily by software, through appropriate algorithms performed by a microcontroller or a digital signal processor. For the sake of clarity, the various processing applied will be decomposed and schematized by a number of separate functional blocks in the form of interconnected circuits. However, this representation is only illustrative, these circuits including common elements in practice may correspond to a plurality of functions generally performed by the same software.

Figure 1:
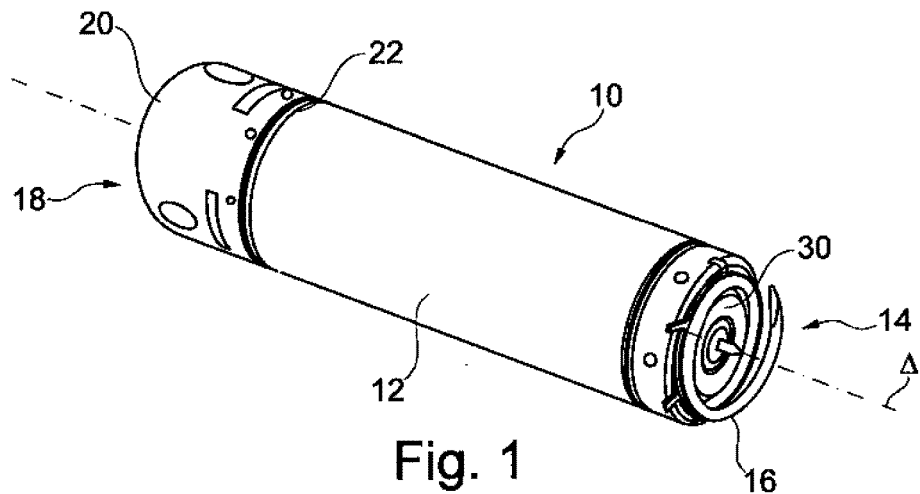
FIG. 1 is an overall perspective view of a leadless capsule.
Figure 2:
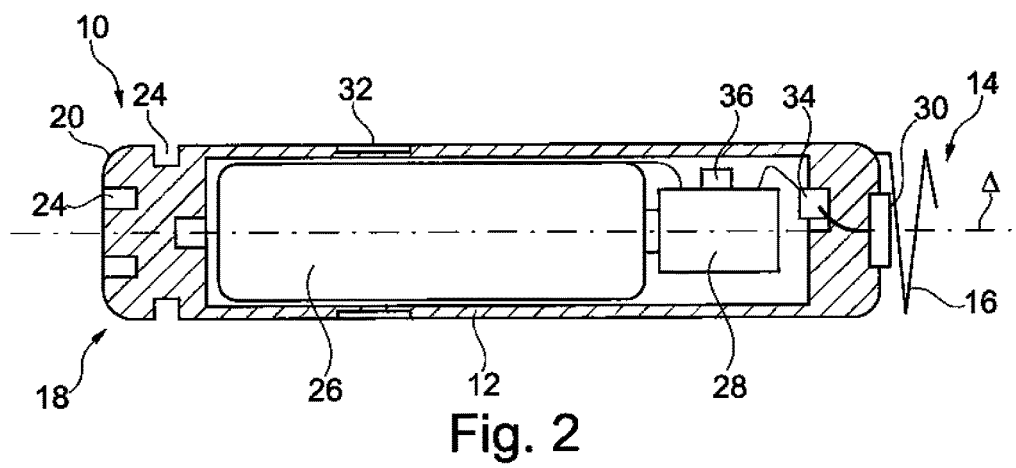
FIG. 2 is a longitudinal sectional view of the leadless capsule of FIG. 1 showing the main internal components which the leadless capsule may include.

FIGS. 1 and 2 show, in perspective and in longitudinal section, an example of a leadless capsule with the various elements the leadless capsule may include.

In these figures, reference 10 designates the leadless capsule generally, formed as a cylindrical tubular body 12 of axis Δ enclosing various electronic and power circuits of the leadless capsule. Typically, the dimensions of such a leadless capsule are a diameter of about 6 mm and a length of about 25 mm.

At a distal end 14, the leadless capsule 10 is provided with a helical anchoring screw 16 for fixing the leadless capsule into the tissue, for example against a wall of a cardiac cavity. The helical anchoring screw can optionally be an active, electrically conductive screw for collecting cardiac depolarization potentials and/or the application of stimulation pulses. A proximal region 18 of the capsule 10 has a rounded, atraumatic end 20 and is provided with gripping means 22 and 24 suitable for implantation or removal of the leadless capsule.

As shown in FIG. 2, the leadless capsule 10 incorporates a battery 26 typically with a volumetric energy density on the order of 0.8 to 2 Wh/cm$^3$, an electronic module 28, a front electrode 30, and optionally a side electrode 32. Feedthroughs such as 34 are used to connect the electrodes 30 and 32 to the electronic module 28.

The electronic module 28 includes electronics for controlling various functions of the leadless capsule 10, for storing collected signals, etc. The electronic module 28 may include a microcontroller and an oscillator generating the necessary clock signals for operation of the microcontroller and communication. The electronic module 28 may also contain an analog/digital converter and a digital storage memory. The electronic module 28 may also contain a transmitter/receiver circuit for exchanging information with other implantable devices by human body communication "HBC" (e.g., intracorporeal communication).

The leadless capsule 10 also typically includes an endocardial acceleration (EA) sensor 36 capable of generating a signal representative of a mechanical activity of the myocardium, for example a sensor in the form of a microaccelerometer interfaced with the electronic module 28.

Figure 3:
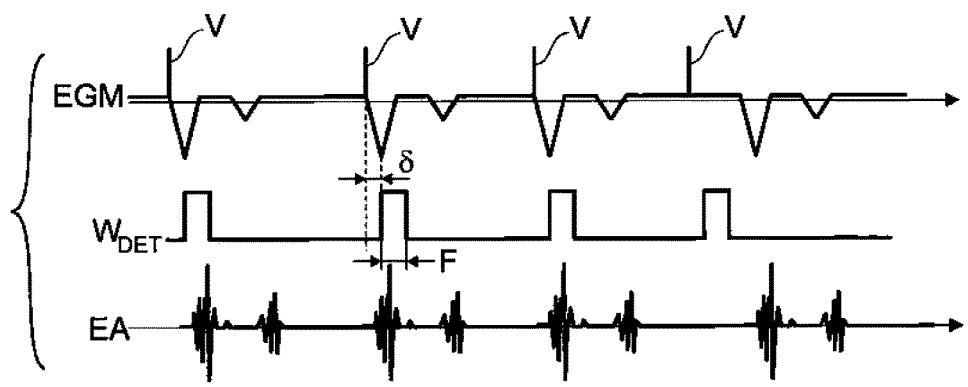
FIG. 3 is a series of timing diagrams illustrating, an electrogram (EGM) signal, the analysis windows for the capture test and the endocardial acceleration EA signal.

FIG. 3 shows a series of timing diagrams illustrating, an electrogram (EGM) signal, analysis windows $W_{DET}$ for the capture test and the EA signal.

After each stimulation (marker V on the EGM indicates stimulated depolarization), the measurement of the EA signal generated by the accelerometer is activated during a window $WET_{DET}$ which is open either immediately after the issuance of the stimulation pulse, or with a delay δ on the order of 5 to 100 ms. The length F of the window $W_{DET}$ is between 75 and 350 ms. Controlling the start time of the capture window $W_{DET}$ and the duration of the capture window is achieved by a sequencing circuit of the microcontroller and by the embedded software which controls the electronic circuits of the leadless capsule 10.

The sensor 36 measuring the EA signal can be a 1D, 2D or 3D accelerometer sensor. Preferably, the sensor is a piezoelectric or capacitive sensor, but other types of sensor (optical, resistive, inductive, etc.) capable of generating a signal correlated to the displacement, velocity or acceleration of the cardiac walls may be used.

Depending on the type of sensor used, the EA signal may or may not contain a DC component.

Figure 4A:
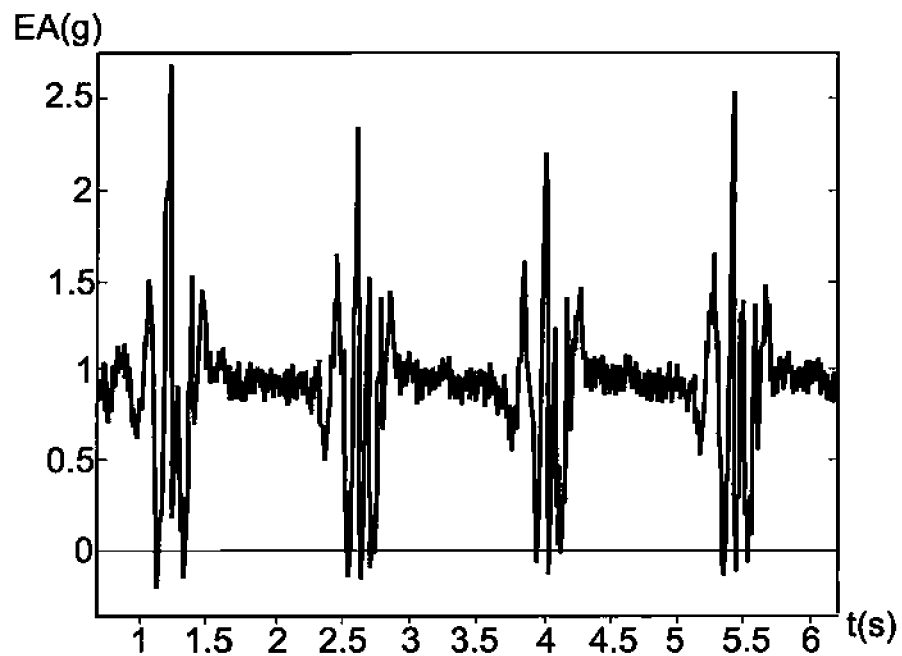
FIGS. 4a and 4b are timing diagrams showing the shape of the EA signal delivered by a sensor more precisely, respectively a capacitive sensor and a piezoelectric sensor.
Figure 4B:
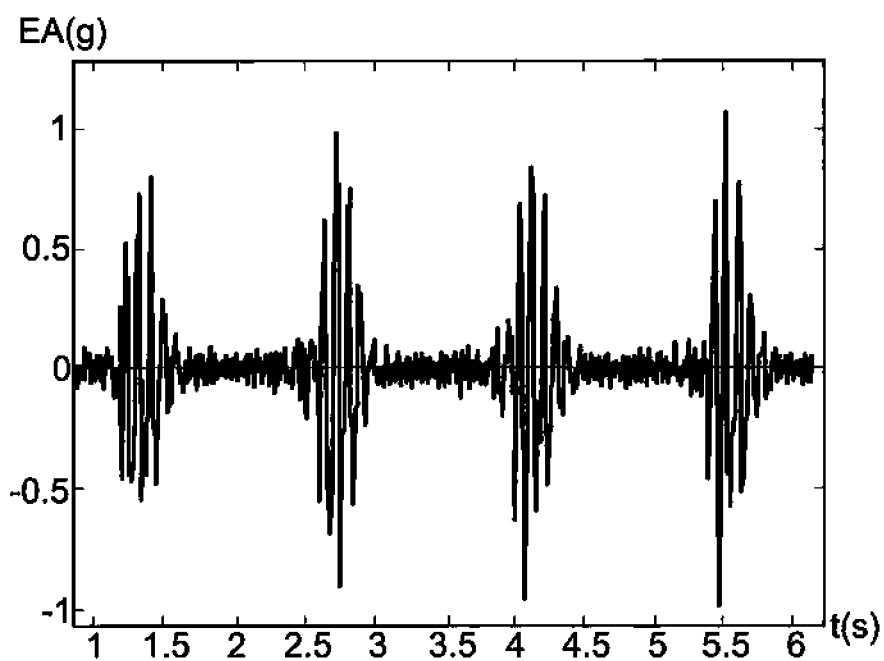

The EA signal generated by a capacitive MEMS sensor (integrated microelectromechanical component) has a general shape illustrated FIG. 4a, with a DC component depending on the orientation of the leadless capsule 10 relative to the direction of gravity. In contrast, the EA signal delivered by a piezoelectric accelerometer shown in FIG. 4b provides a signal with a baseline equal to zero, since by design it ensures the filtering of a DC component.

In either case, the capture test measuring circuit is active only for the duration of the acceleration measuring window, the circuit being totally or partially switched off (muting) the rest of the cardiac cycle. If the latency of the sensor is less than the time between two successive acceleration measurements, it is possible to switch off the circuit and the sensor between two successive measurements of the EA signal.

In the case of a piezoelectric sensor and its interface circuit, the energy consumption is on the order of 100 to 200 nW. If the piezoelectric sensor is activated only for the duration of the $W_{DET}$ window, corresponding to 20 to 50% of the cardiac cycle length, the average consumption of the piezoelectric sensor can be reduced to a value of about 50 to 100 nW.

In the case of a MEMS capacitive sensor, the energy consumption on the order of 300 to 600 nW can be reduced in the same method as above to a value in the range of 150 to 300 nW if the measurement circuit is not activate for the duration of the detection window $W_{DET}$.

Figure 5:
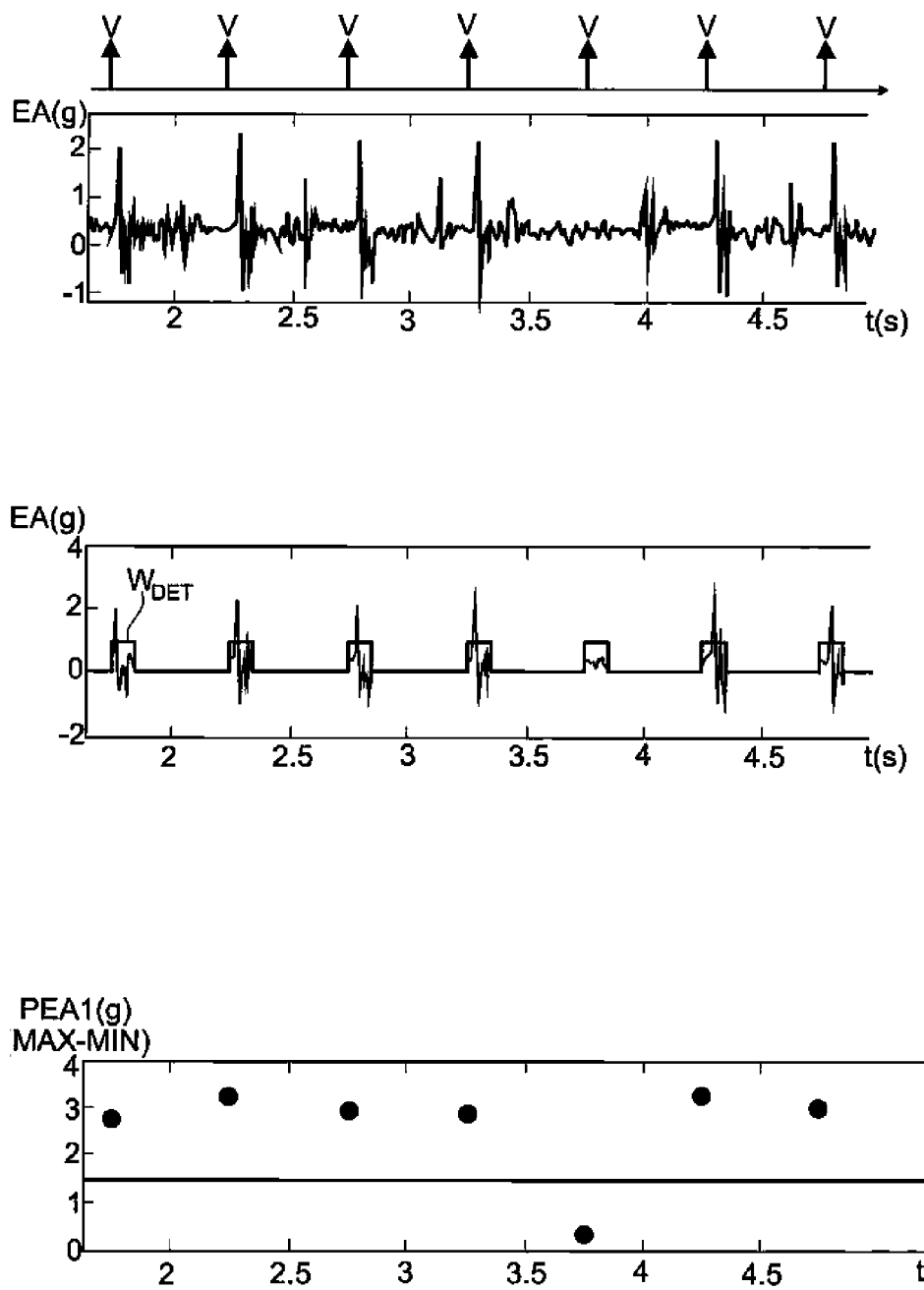
FIG. 5 is a series of timing diagrams illustrative of the known method of operating a capture test.

FIG. 5 shows a series of timing diagrams explaining a known method to operate the capture test. Represented in these timing diagrams, are successively:

V markers of stimulated depolarization;
An endocardial acceleration EA signal;
The EA signal after sampling during the detection periods $W_{DET}$; and
A calculated value of a peak of endocardial acceleration PEA1, i.e., the value of a difference between a maximum and a minimum (in algebraic value) of the EA signal values sampled during the detection window.

The parameter PEA1 is compared with a predetermined threshold and, for example at the fifth cardiac cycle, if this value is less than the threshold, absence of capture is determined.

The parameter PEA1 which is based on a minimum-maximum difference, is very sensitive to measurement noise and to physiological noises generated, for example, by a patient's breathing or sudden movements that result in corresponding movements of the sensor.

Because the parameter PEA1 is very sensitive the capture test is typically not based on an analysis of this single parameter, but is combined with other representative parameters, as in the case of the multivariate analysis described by EP 2412401 A1 cited above.

An embodiment of the invention, proposes to make a capture test from a single indicator which i) requires a minimum of numerical calculations in order to save the energy consumed by a device and ii) is robust to noise, so as to minimize the risk of false capture detections (false positives), which could affect the reliability of the capture test.

An embodiment of the invention uses an indicator value of an average of absolute values of successive measurements of the EA signal sampled during the detection window.

Denoting by $x_i$, with $i=1, \ldots, N$, where N is the number of acceleration measurements delivered by the capsule sensor, and in the case of a piezoelectric sensor (wherein the EA signal varies around a baseline equal to zero), such an indicator value according to an embodiment of the invention can be calculated by:

$$\text{MEAN}_{ABS1} = \frac{1}{N} \sum_{i=1}^{N} |x_i|$$

N may be between 20 and 50 depending on the sampling frequency.

Without impairing the suitability of the indicator, one can avoid the division operation of 1/N, which may be costly in computation time, when using the same number N of samples in each cardiac cycle to calculate the representative indicator $\text{MEAN}_{ABS1}$, which gives:

$$\text{MEAN}'_{ABS1} = \sum_{i=1}^{N} |x_i|.$$

Calculating the representative indicator $\text{MEAN}_{ABS1}'$ is therefore limited to a simple summation of N successive values taken by the signal EA during the window $W_{DET}$ (even if the window contains a number of samples greater than N).

In the case of a MEMS capacitive sensor, the baseline of the acceleration signal depends on the orientation of the capsule relative to the vertical direction. The gravitational acceleration component (severity) is present in the EA signal independently of the acceleration induced by the cardiac motion and results, as explained above in connection with FIG. 4a, in a non-zero baseline present in the EA signal.

The DC component must be removed in the calculation of the indicator value, which then takes the form:

$$\text{MEAN}_{ABS2} = \frac{1}{N} \sum_{i=1}^{N} |x_i - m|$$

where m represents the average value of the baseline of the EA signal.

To simplify the calculation, it is possible to use as an approximation of the value of the baseline of the first value $x_1$ measured during the detection window $W_{DET}$:

$$\text{MEAN}_{ABS3} = \sum_{i=2}^{N} |x_i - x_1|.$$

The indicator $\text{MEAN}_{ABS}$ determined by one of the preceding methods is associated with a criterion of presence/absence of capture for use in a capture verification algorithm. The criteria used may be a simple comparison with a discrimination threshold determined in advance.

Figure 6:
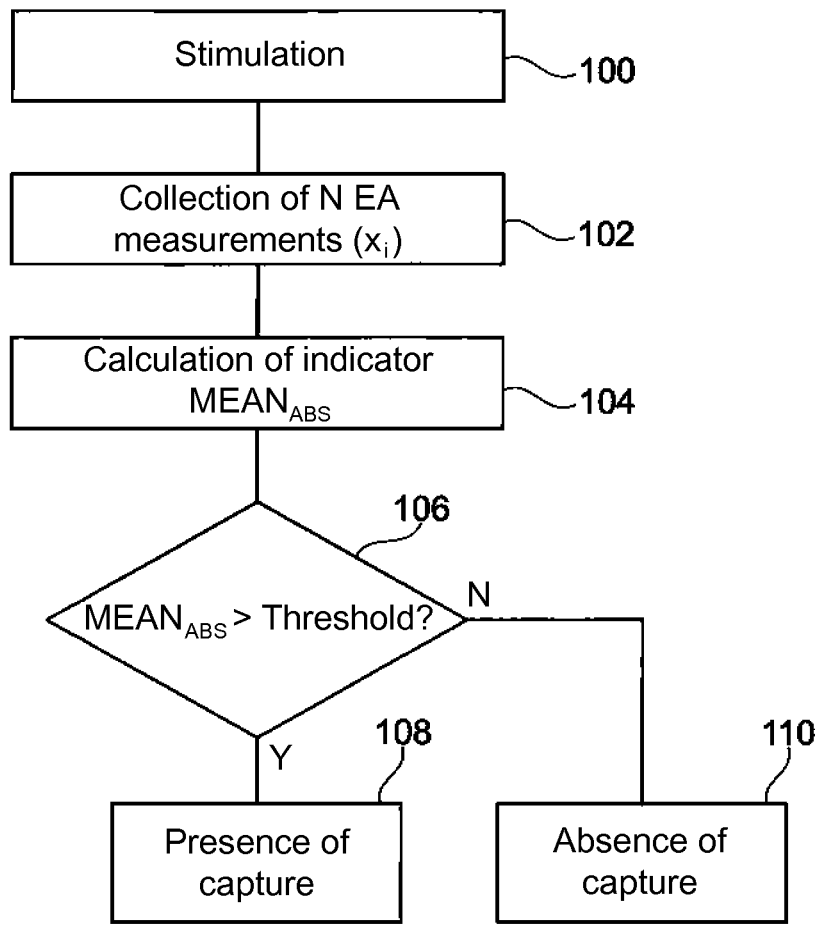
FIG. 6 is a flow chart outlining the main steps of the capture detection method according to an embodiment of the invention.

FIG. 6 is a flowchart summarizing different stages of the capture test.

After stimulation (step 100), the device collects N measurements of the EA signal (values $x_i$) successively sampled within the detection window $W_{DET}$ (step 102). The $\text{MEAN}_{ABS}$ indicator value is then calculated by summing absolute values of the measured values $x_i$ or by summing the absolute values of differences between the measured values $x_i$ and a constant value, reflecting a shift of a baseline with respect to an origin (step 104).

The calculated $\text{MEAN}_{ABS}$ indicator value is then compared with a predetermined threshold (step 106). If the indicator is above the predetermined threshold, then it is determined that there is a presence of capture (step 108); otherwise, it is determined that there is an absence of capture (step 110).

The predetermined threshold used to discriminate between the presence and absence of capture is preferably not a fixed threshold but a threshold calculated automatically, to reflect specific circumstances of a particular patient and a possible evolution of his/her clinical condition over a long term.

A discrimination threshold may be determined during a preliminary initialization phase, as follows.

The device triggers M successive stimuli (typically M=3, 5 or 10 stimuli) with parameters set to deliver a maximum energy, for example a pulse voltage of 5 to 7 V and a pulse width of 1 to 2 ms.

For each stimulation i, $i=1, \ldots, M$, the device calculates the value of the indicator $\text{MEAN}_{ABS}$.

A stimulation threshold $\text{Cap}_{Threshold}$ is then determined by:

$$\text{Cap}_{Threshold} = \frac{\alpha}{M} \sum_{i=1}^{M} \text{MEAN}_{ABS_i}$$

where $\alpha$ is a predetermined reduction factor, for example $\alpha = \frac{1}{2}$, $\frac{1}{3}$ or $\frac{2}{3}$.

$\text{Cap}_{Threshold}$ is the value of the discrimination threshold to be applied to each subsequent capture test.

Figure 7:
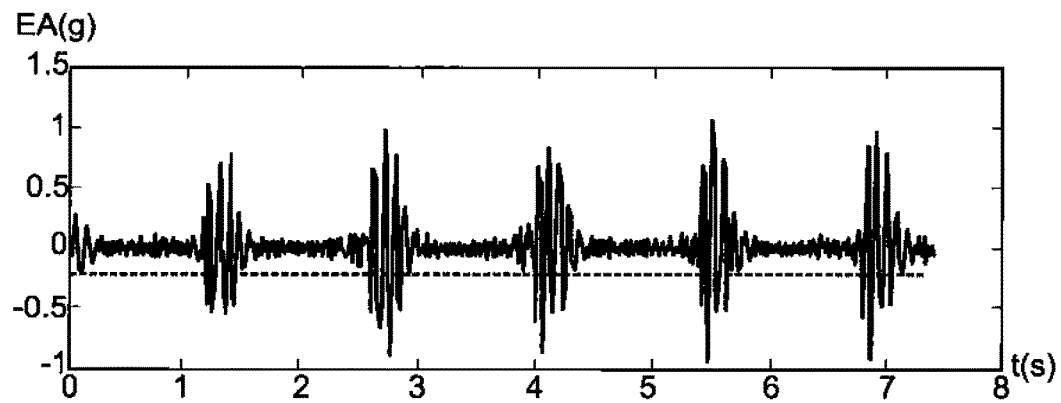
FIG. 7 is a series of timing diagrams illustrative of the method of FIG. 6, to determine the discrimination threshold between capture and no capture.
Figure 7:
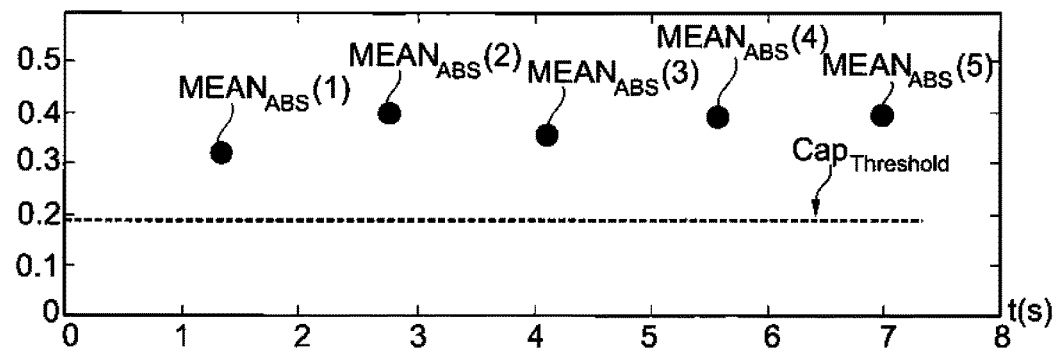

FIG. 7 illustrates an example of determining the discrimination threshold according to this technique, with M=5 stimuli during the initialization phase.

The top timing diagram shows the signal EA obtained as a result of the 5 stimuli, and the bottom timing diagram shows the five corresponding values of the parameter $MEAN_{ABS}(i)$. The five values are averaged and a reduction factor $\alpha=\frac{1}{2}$ is applied to the calculated average, giving a threshold value of approximately 0.185 g (g being the acceleration of gravity).

Figure 8:
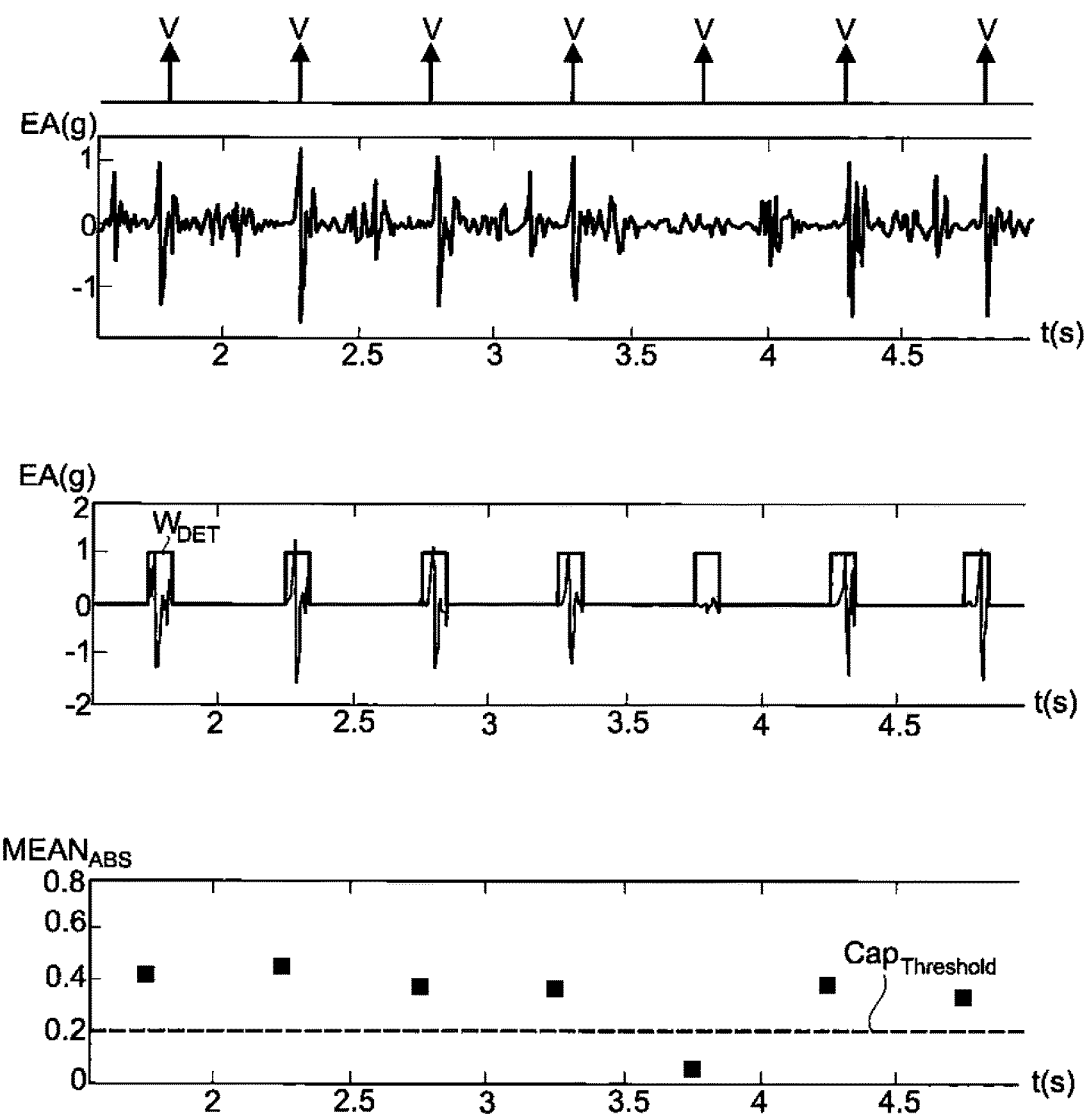
FIG. 8 is a series of timing diagrams corresponding to an exemplary implementation of the invention, after the discrimination threshold has been determined.

FIG. 8 shows an example of using the EA signal for a capture test according to the teachings of the present disclosure. The successive following elements are shown in FIG. 8:

V markers of stimulated depolarization;

An EA signal;

The EA signal after collecting during detection periods $W_{DET}$; and

Calculated parameter $MEAN_{ABS}(i)$.

It can be seen that at the fifth stimuli, at t=3.75 s, the EA signal collected during the corresponding collecting window has very low amplitude.

The value of the $MEAN_{ABS}(5)$ indicator calculated for this window is about 0.04 g while $MEAN_{ABS}$ was approximately 0.4 g for the other stimuli, which caused a capture. The discrimination threshold in this case was set to 0.2 g, and it can be seen that it was possible to clearly distinguish the cycles where a capture is present from the cycles where a capture is not present, with excellent immunity to various noise likely to interfere with the EA signal.

Note that the indicator $MEAN_{ABS}$ is very simple to calculate with a microcontroller, because it is just a sum of N numerical integers.

It is also robust to noise because the summation operation is equivalent to operating a low-pass filter, which greatly reduces the incidence of noise.

Finally, the capture test criterion is particularly simple to implement—a simple comparison between two numeric values to separate a capture zone from an absence of capture zone—with a very large economy of calculation methods.

What is claimed is:

1. An active implantable medical device comprising:
   a housing comprising:
   a ventricular stimulation circuit adapted to deliver stimulation pulses to a ventricle of a patient;
   an acceleration sensor, capable of generating an endocardial acceleration (EA) signal; and
   a ventricular capture detection circuit adapted to detect a presence or absence of a contraction of the ventricle after an application of a stimulation pulse, comprising a processor configured to:
   collect a series of successive EA measurements during a duration of a predetermined temporal window which opens after the application of the stimulation pulse,
   calculate an indicator value based on an average of absolute values of series of the successive EA measurements when the predetermined temporal window ends; and
   compare the indicator value to a predetermined discrimination threshold; and
   determine a presence or absence of ventricular capture depending on whether the indicator value is above or below the predetermined discrimination threshold.

2. The device of claim 1, wherein the indicator value is calculated independently of peak-to-peak values of the EA signal.

3. The device of claim 1, wherein the duration of the predetermined temporal window is between 75 and 350 ms.

4. The device of claim 1, wherein the predetermined temporal window begins between 5 and 100 ms after delivery of the stimulation pulse.

5. The device of claim 1, wherein the processor is further configured to disable the ventricular capture detection circuit after the temporal window ends until the temporal window begins for a next cardiac cycle.

6. The device of claim 5, wherein the ventricular capture detection circuit is disabled between two successive collections of the EA signal generated by the sensor.

7. The device of claim 1, wherein the indicator value is calculated from a constant number of successive EA measurements from one cardiac cycle to another.

8. The device of claim 1, wherein the indicator value is calculated by summing absolute values of the series of successive EA measurements.

9. The device of claim 1, wherein the indicator value is calculated by summing absolute values of respective differences between: i) the series of successive EA measurements and ii) a value which is an average of the series of successive EA measurements.

10. The device of claim 1, wherein the indicator value is calculated by summing absolute values of respective differences between: i) the series of successive EA measurements and ii) a constant base line.

11. The device of claim 1, wherein the indicator value is calculated by summing absolute values of respective differences between: i) the series of successive EA measurements and ii) a value of a first EA measurement of the series of successive EA measurements.

12. The device of claim 1, wherein the processor is further configured to determine a discrimination threshold, wherein determining the discrimination threshold comprises:
   controlling the ventricular stimulation circuit to deliver a series of stimulation pulses with maximum energy;
   calculating an average of the indicator values of the series of stimulation pulses with the maximum energy; and
   applying a reduction factor to the average of the indicator value; and
   issuing a value for the discrimination threshold.

\* \* \* \* \*